United States Patent [19]
Ishikawa et al.

[11] Patent Number: 4,620,146
[45] Date of Patent: Oct. 28, 1986

[54] MICROWAVE MOISTURE SENSOR

[75] Inventors: Hirotoshi Ishikawa; Seiichiro Kiyobe, both of Tokyo, Japan

[73] Assignee: Kogawa Hokushin Electric Corporation, Tokyo, Japan

[21] Appl. No.: 602,594

[22] Filed: Apr. 20, 1984

[30] Foreign Application Priority Data

Apr. 26, 1983 [JP] Japan .................................. 58-73538

[51] Int. Cl.$^4$ ...................... G01B 15/02; G01R 27/26
[52] U.S. Cl. ........................... 324/58.5 A; 324/58.5 R; 343/703
[58] Field of Search ................... 343/703, 781 R, 782, 343/786; 324/58.5 R, 58.5 A, 58.5 B, 58.5 C

[56] References Cited

U.S. PATENT DOCUMENTS

| | | | |
|---|---|---|---|
| 3,156,917 | 11/1964 | Parmeggiani | 343/782 |
| 3,681,684 | 8/1972 | Busker | 324/58.5 A |
| 3,733,609 | 5/1973 | Bartlett | 343/782 |
| 4,423,422 | 12/1983 | Knop | 343/786 |

FOREIGN PATENT DOCUMENTS

| | | | |
|---|---|---|---|
| 9187 | 7/1979 | European Pat. Off. | 324/58.5 R |
| 834045 | 5/1975 | U.S.S.R. | 324/58.5 A |

Primary Examiner—Reinhard J. Eisenzopf
Assistant Examiner—Jose M. Solis
Attorney, Agent, or Firm—Moonray Kojima

[57] ABSTRACT

A microwave moisture sensor comprising a first transmission and reception system comprising first transmission and reception horn antennas disposed in confronting relation with respect to each other and with a movable sheet like measurand disposed therebetween; and a second transmission and reception system comprising a second transmission horn antenna for re-emitting a microwave, as received by the first reception horn antenna against the measurand, and a second reception horn antenna for receiving the microwave emitted by the second transmission horn antenna and having passed through the measurand. The antennas disposed on one side of the measurand are spaced from each other by a distance of $n\lambda \pm \lambda/4$, wherein n is an integer and $\lambda$ is the wavelength of the microwave, in a direction substantially perpendicular to the plane of the measurand.

4 Claims, 9 Drawing Figures

MICROWAVE MOISTURE SENSOR

BACKGROUND OF THE INVENTION

1. Field of Invention

This invention relates to a microwave moisture sensor which operates on the principle that an emitted microwave is attenuated in rotary resonance with water molecules; and more particularly, to such a sensor comprising at least two transmission and reception systems, each comprising a transmission horn antenna and a reception horn antenna, with the antennas which are disposed on one side of a body being measured being spaced a predetermined distance in a direction perpendicular to the plane of the body.

2. Description of the Prior Art

Microwave moisture sensors are known in the art. One example of such a sensor is shown in FIG. 1. The illustrated sensor includes a transmission horn antenna 4 for emitting a microwave supplied from a microwave oscillator 2, through an isolator 1, toward a measurand 3 (that is, an object being measured), such as a sheet of paper, a reception horn antenna 5 disposed in confronting relation to transmission horn antenna 4 with paper sheet 3 disposed therebetween, a transmission horn antenna 6 for re-emitting the microwave, as received by reception horn antenna 5, toward paper sheet 3, and a reception horn 7 disposed in confronting relation to transmission horn 6 with sheet 3 interposed therebetween. Horns 5 and 6 may be interconnected by a coaxial cable (not numbered). The prior sensor also includes a detector (comprising, for example a Schottky diode) 8 which is energized by a local oscillator, not shown, and which supplies a frequency signal having a frequency which is different from that of the signal from microwave oscillator 2. Detector 8 detects the microwave received by reception horn antenna 7. The sensor further comprises a signal processor 9 supplied with a signal from detector 8, and a preset signal indicative of the basis weight of paper sheet 3, and processes these supplied signals based on a predetermined calibration or working curve to generate a moisture percentage signal. Isolator 1, microwave oscillator 2, horn antennas 4,7 and detector 8 are normally housed in a first metal casing. Horn antennas 5,6 are normally housed in a second metal casing.

As illustrated in FIG. 2, the first and second casings 10, and 11, respectively, are disposed in confronting relation on a centrally open frame 12 and jointly constitute a detector head 13. First and second casings 10,11, which may be of metal, synchronously scan or reciprocally travel over an interval or distance between limits $L_1$ and $L_2$, for detecting signals. The scanning direction extends substantially transversely of the moving direction of paper sheet 3, which moves in the direction of arrow A.

While detector head 13 scans sheet 3, the transmission and reception horn antennas are kept at a constant distance l, as shown in FIG. 1, from sheet 3, with the transmission and reception horn antennas 4 and 5, 6 and 7 being equidistant from the travel of the paper sheet 3 as positioned in FIG. 1.

Moisture measurement is effected by the microwave moisture sensor while the interval $L_1$-$L_2$ is being scanned by detector head 13. At this time, a microwave emitted from transmission horn antenna 4 is propagated through a path from transmission horn antenna 4, to paper sheet 3, to reception horn antenna 5, via coaxial cable not numbered to transmission horn antenna 6, to paper sheet 3, to reception horn antenna 7, and is finally detected by detector 8. Signal processor 9 is fed with a signal, as detected by detector 8 and a preset signal, representative of the basis weight of paper sheet 3, and processes the supplied signals based on a calibration or working curve, thereby to generate a moisture percentage signal.

A voltage $V_1$ (of a standing wave) in the propagation path can be derived on the basis of a wave motion from the following equation, provided there is no attenuation in the propagation path.

$$V_1 = V^+ e^{-j\beta x} + \Gamma V^+ e^{j\beta x} \tag{1}$$

wherein $V^+$ is the output voltage of the microwave oscillator, $\Gamma$ is the reflectivity, $\beta$ is the phase constant, and x is the propagation path length from the microwave oscillator. The amplitude signal $|V_1|$ in equation (1) is expressed by following equation (2), while the ratio (standing wave ratio) of the maximum value $|V_{1max}|$ to the minimum value $|V_{1min}|$ of amplitude signal $|V_1|$ is expressed by the following equation (3). The phase, amplitude and other parameters of tne voltage $V_1$ vary with vibrations of paper sheet 3.

$$\begin{aligned}
|V_1| &= |V^+| \left| \frac{(1 + e^{j2\beta x})}{e^{j\beta x}} \right| \\
&= |V^+| |1 + \Gamma e^{j2\beta x}| \\
&= |V^+| \{(1 + \Gamma\cos 2\beta x)^2 + \Gamma^2 \sin^2 2\beta x\}^{\frac{1}{2}} \\
&= |V^+| \{(1 + \Gamma)^2 - 2\Gamma(1 - \cos 2\beta x)\}^{\frac{1}{2}} \\
&= |V^+| \{(1 + \Gamma)^2 - 4\Gamma \sin^2 \beta x\}^{\frac{1}{2}}
\end{aligned} \tag{2}$$

$$\frac{|V_{1max}|}{|V_{1min}|} = \frac{1 + \Gamma}{1 - \Gamma} \tag{3}$$

The conventional microwave moisture sensor is, however, disadvantageous, in that the measurement errors are increased since the detector also detects influences due to vibrations of paper sheet 3 which occur during its movement.

The actual propagation path of the microwave includes, in addition to the illustrated propagation path, paths in which the microwave is reflected between confronting surfaces of casings 10,11, and between these confronting surfaces and sheet 3. Since such additional propagation paths vary due to vibrations of the travelling paper sheet 3, to thereby change the amount of microwaves falling on tne respective reception horn antennas, measurement errors are also increased.

SUMMARY OF THE INVENTION

Accordingly, an object of the invention is to improve the prior art and to overcome the aforementioned and other disadvantages and deficiencies of the prior art.

Another object is to provide a microwave moisture sensor which is less susceptible to influences due to vibrations of a sheet like material being measured, thereby to achieve high measurement accuracy.

The foregoing and other objects are attained by the invention, which encompasses a microwave moisture sensor comprising a first transmission and reception system comprising first transmission horn antenna and first reception horn antenna, disposed in confronting relation to each other, with a sheet like measurand, such as a sheet of paper, disposed movably therebetween; and a second transmission and reception system comprising a second transmission horn antenna for reemitting a microwave as received by the first reception horn antenna, against the measurand, and a second reception horn antenna for receiving the microwave emitted by the second transmission horn antenna and having passed through the measurand. The antennas disposed on one side of the measurand are spaced from each other by a distance which is equal to $n\lambda \pm \lambda/4$, wherein n is an integer and $\lambda$ is the wavelength of the microwave, and in a direction substantially perpendicular to the plane of the measurand.

BRIEF DESCIPTION OF DRAWINGS

DETAILED DESCRIPTION OF PREFERRED EMBODIMENTS

Figure 3:
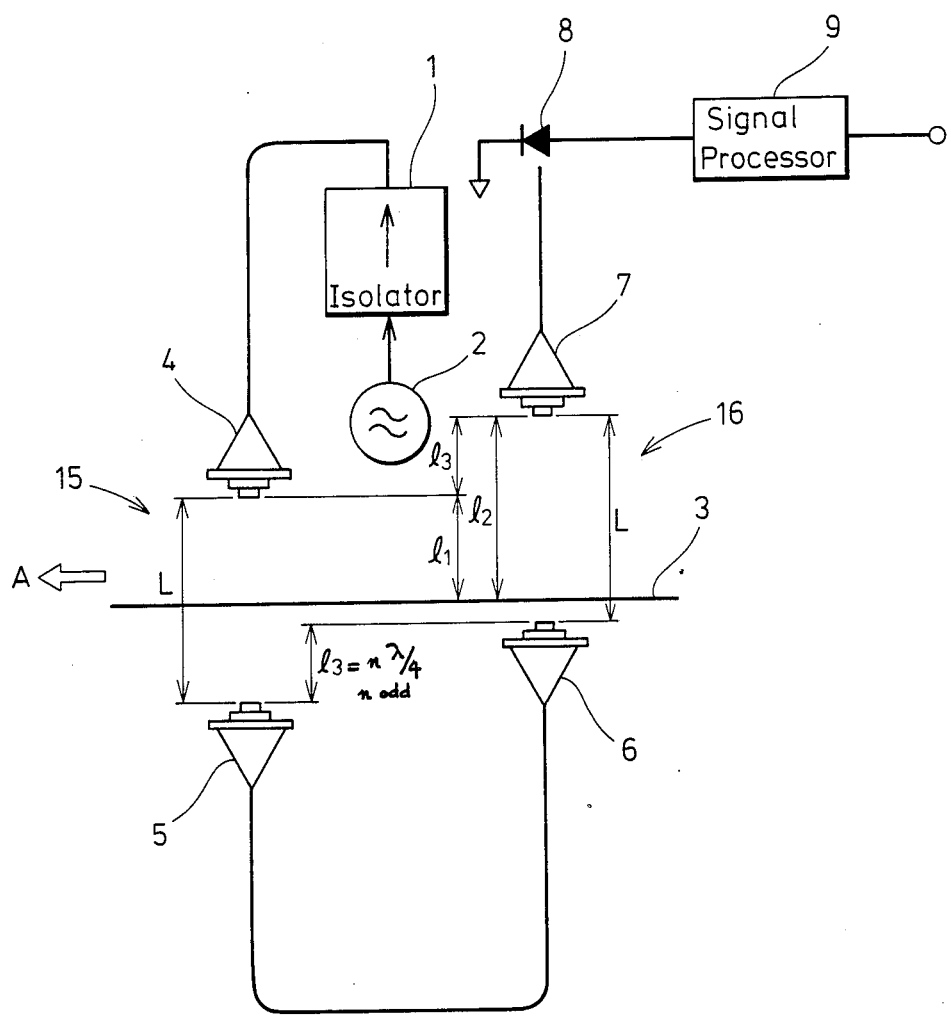
FIG. 3 is a schematic diagram depicting an illustrative embodiment of the invention.

FIG. 3 schematically depicts a microwave moisture sensor embodying the invention. Simiiar or corresponding parts in FIG. 3 are denoted by similar or corresponding reference characters in FIG. 1 and will not be described hereat in detail for sake of clarity of description.

Figure 1:
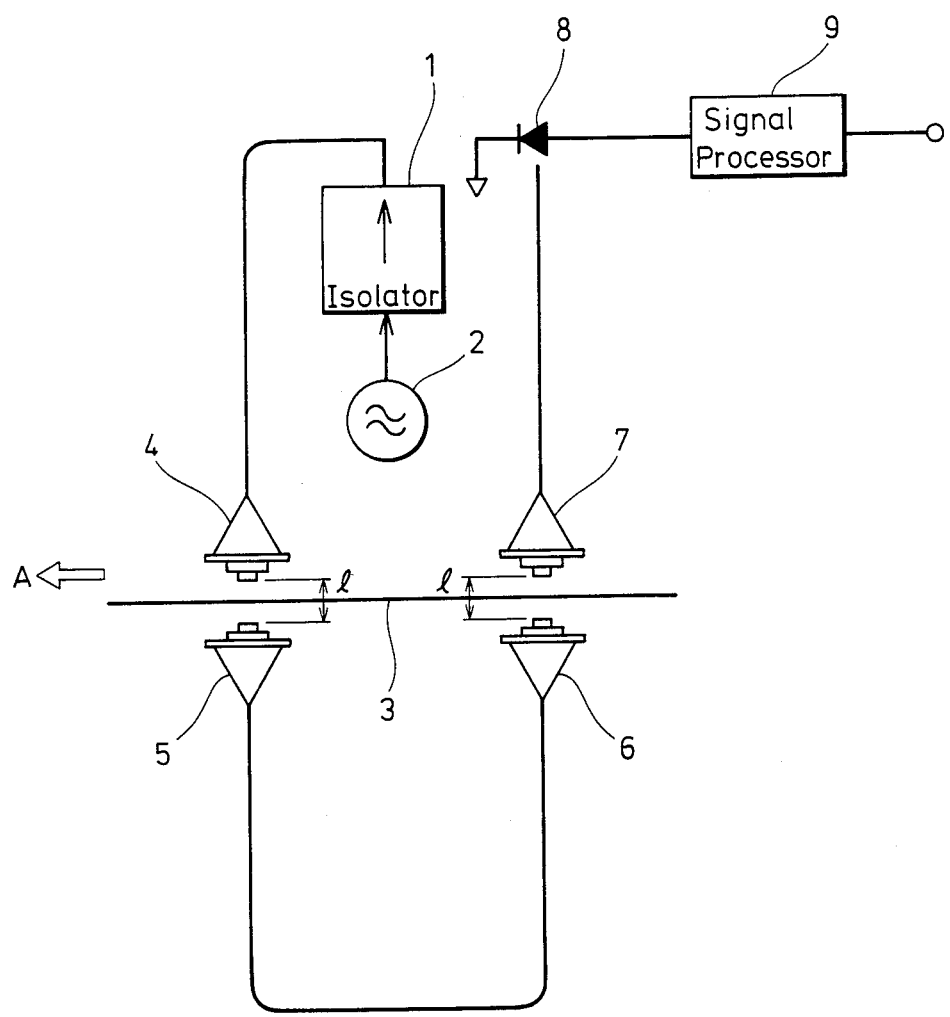
FIG. 1 is a schematic diagram depicting a conventional microwave moisture sensor.

The microwave moisture sensor comprises a first transmission and reception system 15 and second transmission and reception system 16 and other components already described in FIG. 1. The first system 15 comprises a transmission horn antenna 4 spaced a distance $l_1$ from a paper sheet 3 (which is the measurand) and a reception horn antenna 5 spaced a distance L from the transmission horn antenna 4, in confronting relation therewith. The second system 16 comprises a transmission horn antenna 6 for re-emitting a microwave, as received by reception horn 5 of the first system 16, and a reception horn antenna 7 spaced a distance $l_2$ from paper sheet 3 and at a constant distance L from transmission horn 6 in confronting relation therewith. Reception horn antenna 7 and 5 is spaced, respectively, a distance $l_3$ from transmission horn antenna 4 and 6 in a direction substantially perpendicular to the plane of paper sheet 3. Distances $l_1$, $l_2$, and $l_3$ meet the following relationship.

$$l_3 = l_2 - l_1 \div n\lambda \pm \lambda/4 \qquad (4)$$

wherein n is an integer and $\lambda$ is the wavelength of the microwave.

Figure 2:
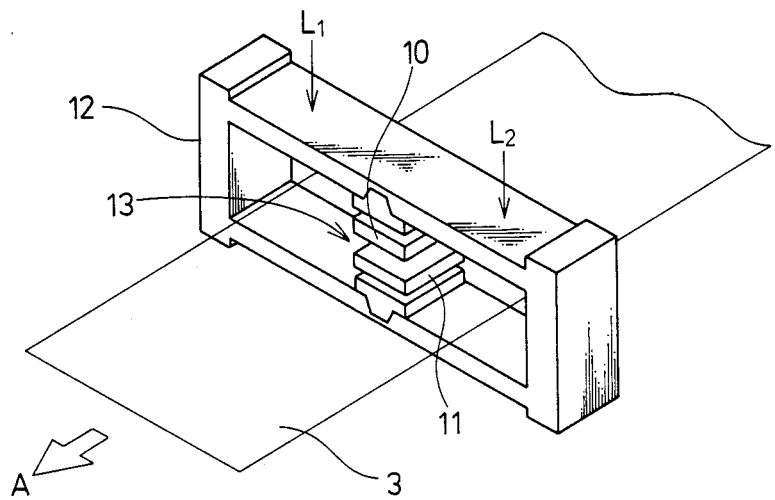
FIG. 2 is a perspective view depicting a centrally open frame wherein a detector head of a sensor is disposed.
Figure 4:
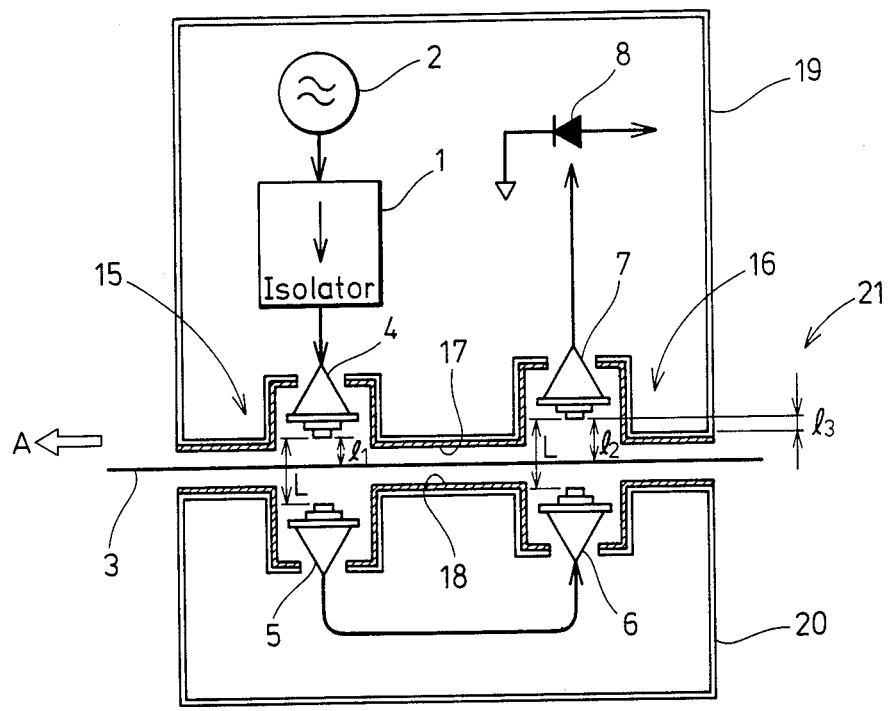
FIG. 4 and FIG. 5 are side and front elevational views of a detector head of the embodiment of FIG. 3.

As illustrated in FIG. 4, transmission and reception systems 15 and 16, are housed in casings 19,20, which may be of metal, having confronting surfaces 17,18 made of a wave absorber, such as comprising a mixture of epoxy paint and brass powder. The casings 19,20 are mounted in a centrally open frame, such as shown in FIG. 2, and jointly constitute a detector head 21, which is used for scanning sheet 3, for a predetermined distance, transversely across the paper sheet.

Figure 5:
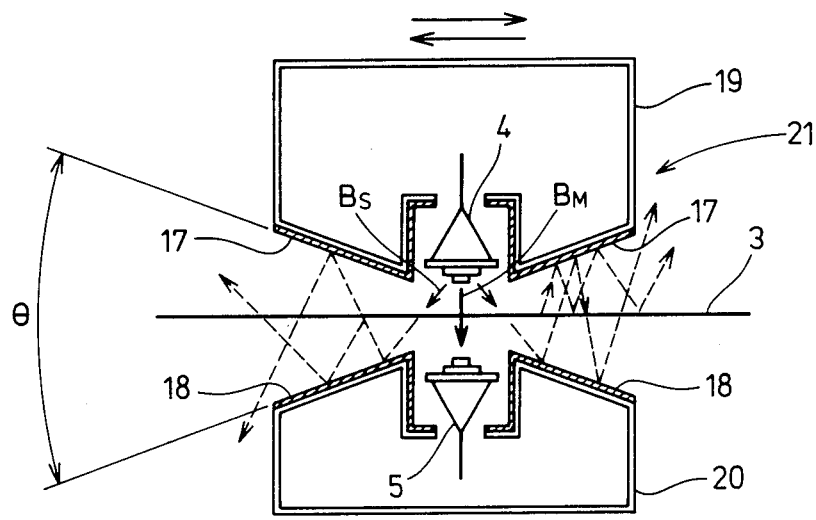

FIG. 5 shows a cross section of casings 19,20, taken along the direction of travel (see arrow A in FIG. 4) of paper 3. As shown in FIG. 5, confronting surfaces 17 of casing 19, are inclined at angle $\theta$ with respect to the confronting surface 18 of casing 20.

Moisture measurement is effected by the microwave moisture sensor while a predetermined distance over paper 3 is being scanned by detector head 21. At this time, a microwave emitted from transmission horn antenna 4, is propagated through a path from transmission horn antenna 4, to paper 3, to reception horn antenna 5, then via a coaxial cable, not numbered, to transmission horn antenna 6, to paper 3, to reception horn antenna 7, and is finally detected by detector 8.

Since equation (4) is established for each transmission and reception system, reception horn antenna 7 can be regarded as substantially detecting the sum $|V_1| + |V_2|$, of the amplitude signal $|V_1|$ defined by equation (2) and the amplitude signal $|V_2|$ defined by equation (5), the signal $|V_2|$ is $\lambda/4$ out of phase with signal $|V_1|$.

$$|V_1| = |V^+| \{(1 + \Gamma)^2 - 4\Gamma\sin^2(\beta x + 90°)\}^{\frac{1}{2}} \qquad (5)$$

$$= |V^+| \{(1 + \Gamma)^2 - 4\cos^2\beta x\}^{\frac{1}{2}}$$

Therefore, the ratio of the maximum value $|V_{3max}|$ to the minimum value $|V_{3min}|$ of a signal detected by detector 8 is given by equation (6).

$$\frac{|V_{1max}|}{|V_{1min}|} = \frac{\sqrt{1 + \Gamma^2}}{1} = \sqrt{1 + \Gamma^2} \qquad (6)$$

Equations (3) and (6) are indicative of variations of the detected signal at the time the path lines (i.e. path of travel) of paper sheet 3 is varied. Since $0 < \Gamma < 1$, the relationship $(1+\Gamma)/(1-\Gamma) > \sqrt{1+\Gamma^2}$ exists. Comparison of the equations (3) and (6) indicates that with the inventive microwave moisture sensor, the detected signal has a small amplitude with respect to vibrations of paper sheet 3. That is to say, the inventive microwave moisture sensor has good path line characteristics.

Where the antennas in the transmission and reception systems 16,15 meet the following relationship (7), the sensor can detect signals of good path line characteristics.

$$l_1 - l_2 \div n\lambda \pm \lambda/4 \qquad (7)$$

Figure 6A:
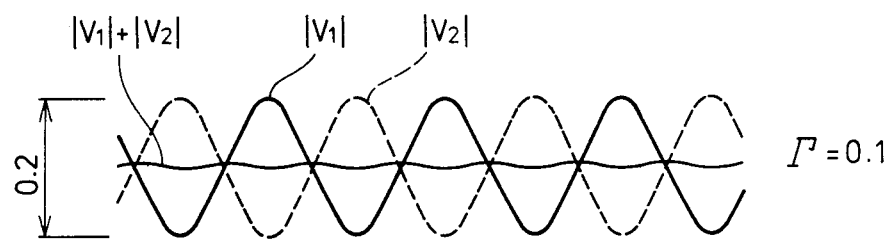
FIGS. 6A, 6B and 7 are diagrams depicting operation of the embodiment.
Figure 6B:
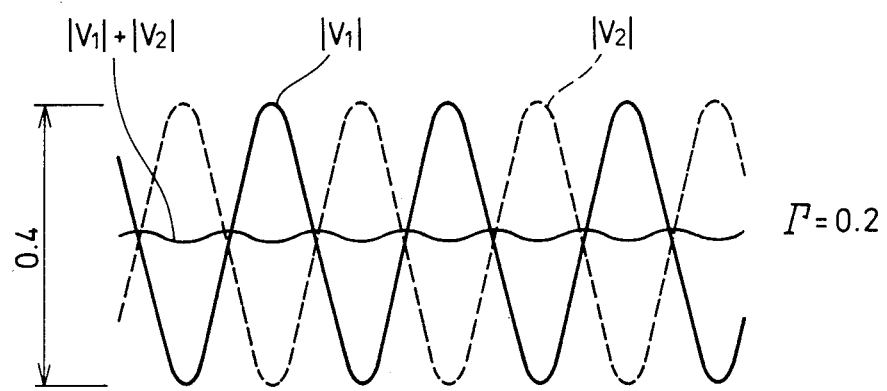

FIGS. 6A and 6B illustrate the relationship between the amplitude signals $|V_1|$, $|V_2|$ and the signals $|V_1| + |V_2|$ detected by detector 8. FIG. 6(A) shows the relationship at the time the reflectivity $\Gamma$ is 0.1. FIG. 6(B) shows the relationship at the time the reflectivity $\Gamma$ is 0.2. FIGS. 6(A) and 6(B) indicate that the inventive microwave moisture sensor has good path line characteristics.

Operation of the embodiment, and especially the multipaths taken by the microwave, is now explained with reference to FIG. 5. The microwave emitted from antenna 4 against paper 3 and passing through the above described path is main beam $B_M$. Side beams $B_S$ emitted from antenna 4 are either absorbed by the wave absorbing confronting surfaces 17,18; or are led out of casings 19,20, after going through repeated reflections between confronting surfaces 17,18 and paper 3, and also between the confronting surfaces 17,18, as shown by the broken line arrows in FIG. 5.

The amounts of microwaves falling on antenna 5,7 are not affected by a spread around the transmitted column of main beam $B_M$, which is coextensive with the open ends of the antennas, and a moisture signal g (MW) is rendered, irrespective of the size of the paper sheet being measured (thus resulting in a substantially reduced measurement area). Hence, signal characteristics, due to the sheet like paper, agree with the calibration or working curve determined by using paper of a brand to be measured which is cut to size.

Figure 7:
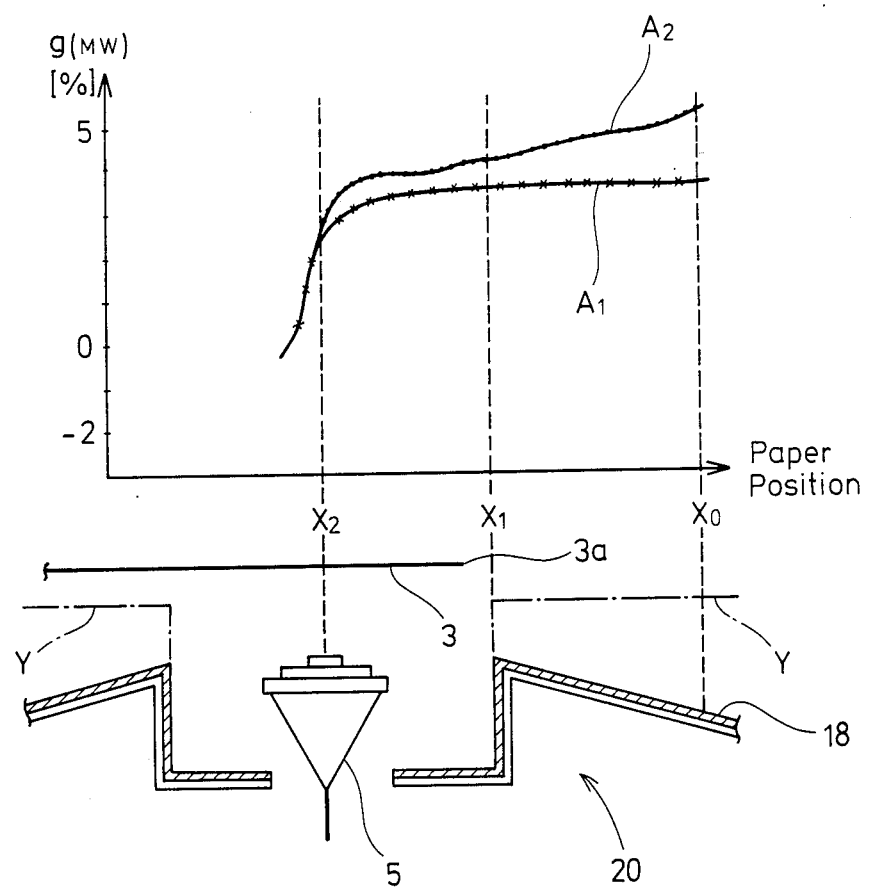

FIG. 7 illustrates paper position characteristic in the inventive sensor. The vertical axis is indicative of a moisture signal g (MW). The horizontal axis is indicative of the position of sheet 3 between the casings. A characteristic curve $A_1$ is drawn by plotting moisture signals g (MW) when an end 3a of paper 3 is moved from position $X_0$ to $X_1$ to $X_2$. Characteristic cuve $A_1$ shows that when paper sheets having widths $2\overline{X_0X_2}$ and $2\overline{X_1X_2}$ are positioned with their centers aligned with the position $X_2$, the moisture signal g(MW) remains unchanged regardless of the different paper widths. Stated in a different way, the microwaves which are repeatedly reflected between positions $X_0$, $X_1$, that is, the microwaves reflected between the confronting surfaces 17,18 and the paper sheet 3, and between the confronting surfaces 17,18, do not fall on reception horn antenna 5. Hence, the moisture signal is not affected by differences between sizes of measurands.

A characteristic curve $A_2$ is representative of a conventional microwave moisture sensor (the confronting surface of casing 20 is indicated by dot-and-dash line Y).

Figure 8:
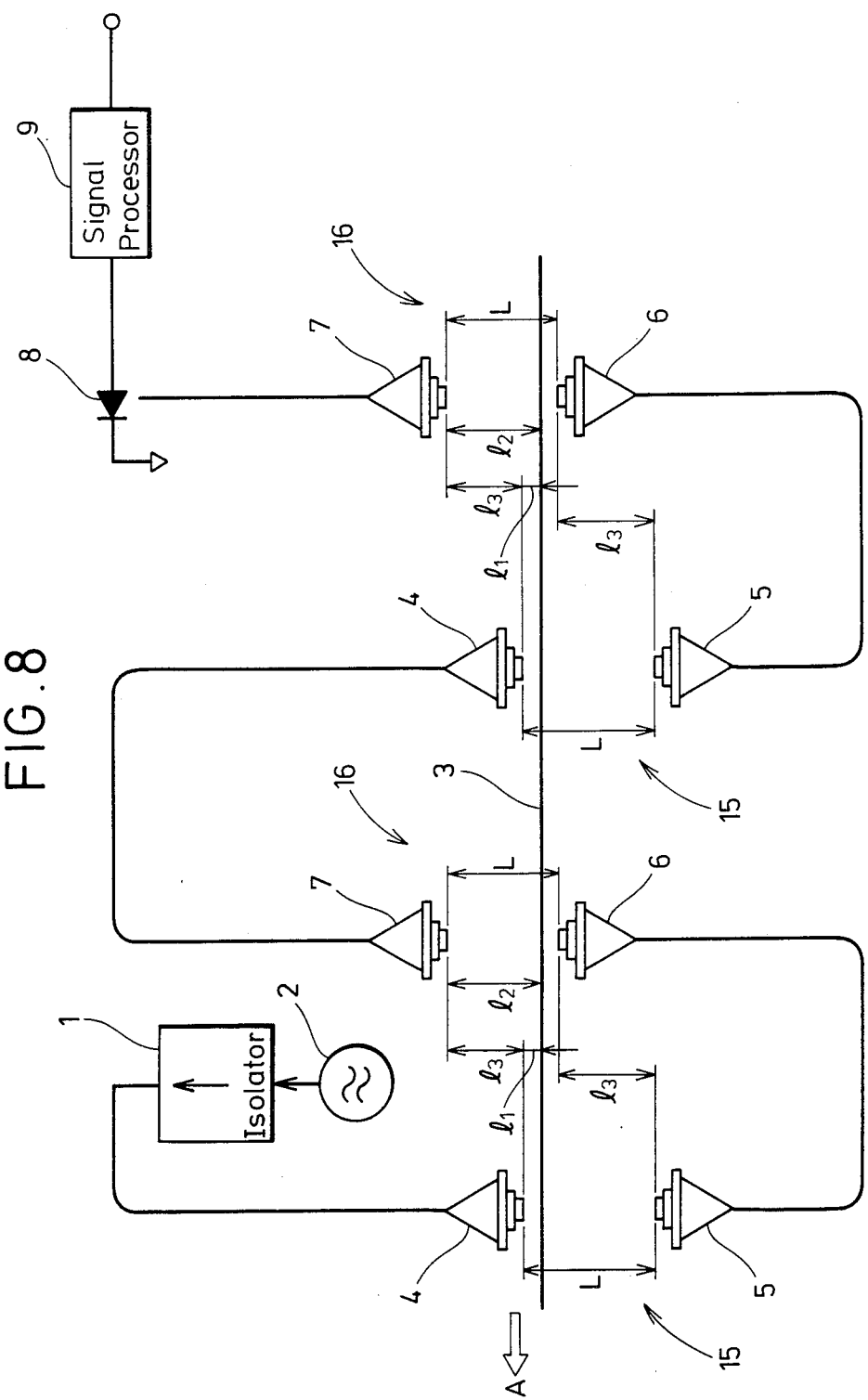
FIG. 8 is a schematic diagram depicting another illustrative embodiment of the invention.

FIG. 8 depicts another illustrative embodiment. Identical and corresponding components in FIG. 8 are denoted by identical and corresponding characters in FIGS. 1 and 3, and will not be described hereat in detail for sake of clarity of description. The sensor in FIG. 8 comprises two sets of transmission and reception systems 15,16, to provide a propagation path wherein a main microwave beam, supplied by oscillator 2, through isolator 1, and emitted from leftmost transmission horn antenna 4 against paper sheet 3, passes through paper sheet, four (4) times, before the microwave is detected by detector 8.

The detecting sensitivity of the sensor of FIG. 8 is thus increased because of the increase, i.e. doubling, of the two systems in the manner depicted.

With the microwave moisture sensor of the invention, there are provided at least two transmission and reception systems, each comprised of transmission and reception horn antennas. The antennas are disposed on one side of a measurand (i.e. object being measured) at a prescribed distance from each other and in a direction which is perpendicular to the plane of the measurand. This arrangement reduces any adverse influence due to vibrations of the measurand and thereby results in an increased measurement accuracy.

The confronting surfaces of the casing which constitute the detector head are wholly or partly inclined with respect to each other, and are covered with a wave absorber. This also reduces any adverse influence due to vibration of the measurand.

The foregoing description is illustrative of the principles of the invention. Numerous modifications and extensions thereof would be apparent to the worker skilled in the art. All such modifications and extensions are to be considered to be within the spirit and scope of the invention.

What is claimed is:

1. A microwave moisture sensor for sensing moisture content in a sheet like measurand having a plane surface by measuring the attenuation of microwave passed through said measurand, comprising at least a first transmission and reception system for emitting a microwave against said measurand and receiving said microwave having passed through said measurand and being attenuated thereby, said first transmission and reception system comprising first transmission horn antenna and first reception horn antenna spaced in confronting relation with respect to each other by a constant distance, with said measurand disposed therebetween;

a second transmission and reception system comprising a second transmission horn antenna disposed on the same side of said measurand in which said first reception horn antenna is disposed, for re-emitting said attenuated microwave as received by said first reception horn antenna against said measurand, and a second reception horn antanna spaced in confronting relation from said said second transmission horn antenna by said constant distance, for receiving said microwave emitted from said second transmission antenna and having passed through said measureand and being attenuated thereby, wherein the offset between antennas at the same side of the measurand, measured in a direction perpendicular to the measurand plane, is equal to an odd multiple of quarter lambda, wherein lambda is the wavelength of said microwave; and signal processor means for processing signals from said second reception horn with a preset signal indicative of the moisture basis weight of said measurand and predetermined moisture calibration data, thereby to generate a moisture percentage signal which is substantially unaffected by vibration of the measurand.

2. The sensor of claim 1, wherein said first and second transmission and reception systems, each comprise first and second casings; said first casing housing said first transmission horn antenna and said second reception horn antenna; said second casing housing said first reception horn antenna and said second transmission horn antenna; said first and second casings being disposed in confronting relation with respect to each other, with said measurand disposed therebetween and having confronting surfaces inclined with respect to each other.

3. The sensor of claim 2, wherein said confronting surfaces of said first and second casings comprise a wave absorber.

4. The sensor of claim 1, further comprising a third and fourth transmission reception system, each comprising transmission horn antenna and reception horn antenna arranged with the transmission antenna of the one system being connected to the reception antenna of the next adjacent system.

* * * * *

UNITED STATES PATENT OFFICE
CERTIFICATE OF CORRECTION

Patent No. 4,620,146                    Dated  October 28, 1986

Inventor(s)  Hirotoshi Ishikawa; Seiichiro Kiyobe

It is certified that error appears in the above-identified patent and that said Letters Patent are hereby corrected as shown below:

Change the name of the assignee from "Kogawa Hokushin

Electric Corporation" to ---- Yokogawa Hokushin

Electric Corporation---

Signed and Sealed this

First Day of September, 1987

*Attest:*

DONALD J. QUIGG

*Attesting Officer*          *Commissioner of Patents and Trademarks*